US012589424B2

(12) United States Patent     (10) Patent No.:   US 12,589,424 B2
Lapin et al.            (45) Date of Patent:     Mar. 31, 2026

(54) DEVICE AND METHOD FOR UNWINDING AND INSPECTION OF METALLIC STRIP COILS

(71) Applicant: DANIELI & C. OFFICINE MECCANICHE S.P.A., Buttrio (IT)

(72) Inventors: Dmytro Lapin, Manzano (IT); Illya Synelnykov, Manzano (IT)

(73) Assignee: DANIELI & C. OFFICINE MECCANICHE S.P.A., Buttrio (IT)

( * ) Notice: Subject to any disclaimer, the term of this patent is extended or adjusted under 35 U.S.C. 154(b) by 264 days.

(21) Appl. No.: 18/271,179

(22) PCT Filed: Jan. 6, 2022

(86) PCT No.: PCT/IB2022/050078
§ 371 (c)(1),
(2) Date: Jul. 6, 2023

(87) PCT Pub. No.: WO2022/149078
PCT Pub. Date: Jul. 14, 2022

(65) Prior Publication Data
US 2024/0299999 A1     Sep. 12, 2024

(30) Foreign Application Priority Data
Jan. 7, 2021    (IT) ........................ 102021000000239

(51) Int. Cl.
*B21C 47/18*       (2006.01)
*B21C 51/00*       (2006.01)
         (Continued)

(52) U.S. Cl.
CPC .............. *B21C 47/18* (2013.01); *B21C 51/00* (2013.01); *B65H 16/106* (2013.01); *G01N 33/20* (2013.01)

(58) Field of Classification Search
CPC ........ B65H 2301/415095; B65H 16/00; B65H 16/106; B65H 18/00; B65H 23/18;
            (Continued)

(56) References Cited

U.S. PATENT DOCUMENTS 2,880,778 A *   4/1959   Spangler ................. B21C 47/16
                                    242/562
3,010,672 A     11/1961   Cecil, Jr.
                   (Continued)

FOREIGN PATENT DOCUMENTS

CA        1327904 C   *   3/1994    ......... B21B 15/0007
DE        621290 C   *   11/1935
                   (Continued)

OTHER PUBLICATIONS

International Search Report for PCT/IB2022/050078 dated May 12, 2022 (3 pages).
                   (Continued)

*Primary Examiner* — Victoria P Augustine
*Assistant Examiner* — Ermia E. Melika
(74) *Attorney, Agent, or Firm* — Tutunjian & Bitetto, P.C.

(57) ABSTRACT

The invention relates to a device for unwinding a coil of a metal strip including a bogie translatable back and forth along a guiding system; a blocking system which is arranged on said bogie and which contains a first and a second shaped element, wherein the first shaped element is a roller, preferably an idle roller; an actuating system for modifying the distance between the two shaped elements, for defining an intercepting position and a gripping position of the strip; and an element for detaching the strip from the coil provided on the first shaped element. A relative method of unwinding and inspecting a metal strip is also described, in particular used to check the state of wear of rolling cylinders used for producing the inspected strip.

17 Claims, 2 Drawing Sheets

(51) Int. Cl.
B65H 16/10 (2006.01)
G01N 33/20 (2019.01)

(58) Field of Classification Search
CPC ........ B65H 20/00; B65H 20/16; B65H 20/36;
B65H 2701/173; B65H 2701/1732; B65H
35/0006
USPC .... 242/532, 532.2, 532.4, 532.5, 563, 564.3
See application file for complete search history.

(56) References Cited

U.S. PATENT DOCUMENTS

| | | | | | |
|---|---|---|---|---|---|
| 4,840,320 | A | * | 6/1989 | Shigeta | B65H 19/1873 |
| | | | | | 242/562.1 |
| 4,848,691 | A | * | 7/1989 | Muto | B65H 19/29 |
| | | | | | 156/506 |
| 5,096,134 | A | * | 3/1992 | Sakano | B65H 19/105 |
| | | | | | 242/562.1 |
| 5,524,844 | A | * | 6/1996 | McCormick | B65H 19/102 |
| | | | | | 242/910 |
| 6,808,581 | B2 | * | 10/2004 | Kuta | B65H 19/105 |
| | | | | | 242/555.3 |
| 2009/0208093 | A1 | | 8/2009 | Mauuary | |

FOREIGN PATENT DOCUMENTS

| | | | | | |
|---|---|---|---|---|---|
| DE | 1020595 | B | * | 12/1957 | ............. B21C 47/34 |
| DE | 4018950 | A1 | | 12/1991 | |
| DE | 202019103848 | U1 | * | 9/2019 | ............. B21C 47/16 |
| EP | 0284918 | A2 | | 10/1988 | |
| EP | 1102647 | B1 | * | 3/2003 | ............. B21C 47/34 |
| GB | 988334 | | | 4/1965 | |
| IT | 102014902227353 | | | 7/2015 | |
| RU | 2679810 | C1 | | 2/2019 | |
| WO | 2015111028 | A1 | | 7/2015 | |

OTHER PUBLICATIONS

Written Opinion of the International Searching Authority for PCT/IB2022/050078 dated May 12, 2022 (6 pages).
Office Action issued in corresponding Russian Patent Application No. 2023120327/05(044116) dated Mar. 29, 2024 (10 pgs).
Search Report issued in corresponding Russian Patent Application No. 2023120327/05(044116) dated Feb. 14, 2024 (2 pgs).

* cited by examiner

DEVICE AND METHOD FOR UNWINDING AND INSPECTION OF METALLIC STRIP COILS

TECHNICAL FIELD

The invention pertains to the field of inspecting metal strip coil surfaces, providing a system and method for unwinding the coil in order to prepare the metal strip for inspection. Metal strips can be rolled strips of steel, aluminium, copper or metal alloys, whether ferrous or non-ferrous, generally belonging to the steel industry.

PRIOR ART

Normally once rolled and in any case between the different steps of the production process, metal strips are stored and transported in the form of coils. The greater the thickness of the strip, the greater the yield strength and consequently the resistance to unwinding which said strip opposes when, for its use and for its qualitative inspection it must be unwound from the coil. Inspections are necessary, for example, to assess the state of wear of the rolling cylinders which directly affects the quality of the strips being rolled. Such a check must not only allow the outer or convex side of the strip to be inspected, but also its concave side, i.e., the inner side.

After unwinding, the strip tends to retain its coil set, making inspection difficult. The known type of strip unwinding systems envisage devices for this purpose, for example pairs of rollers or boards, suitable for straightening the strip, which however have the disadvantage of coming into direct contact with the strip, damaging the surface and risking ruining the surface quality.

The prior art proposes several devices for unwinding metal strips. A system is described in document GB 988,334 of 1965 (see FIG. 1) which positions a mandrel 110 with a coil 112 near a pivoting element 124 placed on a base 126. The strip end 114, corresponding to the last section wound and therefore to the tail of the strip, is raised and guided by a blade 120 (actuatable by a relative articulated arm 121) between a pair of rollers 116, 118 whose distance is adjustable by a pneumatic cylinder 122, which moves the roller 118 with respect to the fixed roller 116. When the strip 114 is inserted, the rollers 116, 118 are approached, grasping the strip 114. The pivoting element 124 is rotated, thus spacing the rollers 116, 118 from the coil 112. The toothed roller mechanism 117, 119 engaging with the gripping rollers 116, 118, acting as a dragger, allows the rotation of the roller system so as to carry the strip 114, which is helped in unwinding by the rotation of the coil 112 by the mandrel 110 in direction A. The proposed solution has some disadvantages, in particular that the inspection of the strip would only be possible on the outer side (arrow V) and that the strip is in close contact with the rollers of the unwinding system as it is unwound.

Document WO 2015/111028 A1 (see FIG. 2) instead limits the contact between the strip and the unwinding device to only contact with a portion of the strip and also allows inspection of the inner surface of said strip, but requires a rather complex mechanism. This solution also involves positioning a mandrel 210 with a coil 212 near a system which detaches the strip end 214a from the coil. In this regard, a blade plate 220a is included which detaches and spaces the strip end 214a from the coil. The plate 220a is positioned on a roller 218a which together with the plate forms the end of a pivoting arm 221a. After the strip end 214a is detached, the arm provided with roller 218a and plate 220a accompanies the strip in its unwound position 214b up to reaching above a second fixed roller 216 where the movable roller occupies the position 218b and the arm the position 221b. The strip 214b transits between the two rollers 216, 218b which, optionally together with a retaining table 127, prevent the return of the strip 214b to its curved shape. A gripping element mounted on a bogie 230 translatable along guide 228 in direction B and not specified in more detail grasps the strip end. The movement of the bogie 230 and the respective rotation (arrow A) of the coil involve the unwinding of the strip from the coil 212. During this movement, the rollers 216 and 218b are distanced from the strip 214b. The system allows the inspection of the inner surface of the strip (arrow V).

Italian application IT 102014902227353 proposes similar relatively complex systems for detaching strips from coils and guiding them between two rollers for the purpose of their unwinding using roller systems and orientable plates.

The above prior-art systems have one or more of the following drawbacks: they require contact between the unwinding device and the strip, in particular they obtain a contact which occurs along the entire unwound piece, with the risk of modifying the surface of the latter, they require complex devices with many components also to adapt to the different characteristics of different strips in terms of resistance to unwinding and do not always allow inspection of the inner or concave surface of the strip.

Other systems for unwinding coils are disclosed in EP 0 284 918 A2, DE 40 18 950 A1, U.S. Pat. No. 3,010,672 and US 2009/0208093 A1 of which only the latter relates to the inspection of coils.

SUMMARY OF THE INVENTION

The object of the invention is to overcome the aforesaid drawbacks and to propose an unwinding device for coils of metal strips which allows the inspection of the strip which is not only an alternative to those existing in the state of the art, but also simpler in its construction and operation. A further object of the invention is to find a device according to the above, which is suitable to be used with strips of different thickness and unwinding resistance, thus with strips which tend to more or less maintain the curved conformation.

A further object of the invention is to provide a device for unwinding coils, which also allows inspection of the inner side of the strip and which reduces as much as possible the contact between portions of the strip and elements of the device itself, in order to propose a method for unwinding coils and a relative inspection system. Further objects or advantages of the invention will be apparent from the following description.

In a first aspect of the invention, the object is achieved by a device for unwinding a coil of a metal strip comprising:
  (a) a bogie and a guiding system wherein the bogie is translatable back and forth along the guiding system;
  (b) a blocking system which is arranged on said bogie and which contains a first shaped element which is a roller, and a second shaped element, in particular a second roller;
  (c) an actuating system, for modifying the distance between said first and second shaped elements, which is preferably arranged on said bogie, for defining an intercepting position of a strip end between said two shaped elements when spaced and a gripping position of said strip end by said two shaped elements when close together; and (d) an element for detaching said strip end from the coil provided on the first shaped element.

With a minimum of elements, the device according to the invention allows unwinding a metal strip from a coil wherein the single contact between the strip and the device concerns the strip end. The translation of the bogie and the traction thus applied to the unwound strip ensures that the strip does not return to its coil set. With respect to the state of the art disclosed in GB 988,334 the strip is not dragged through two rollers to distance it from the coil, but the strip end is grasped at a point between the two shaped elements (which can be of the rollers) and the strip does not pass through these two components to be unwound thus avoiding contact with the strip over practically the entire unwound length, and limiting contact to the strip end. Among the actuated rollers of the aforementioned state of the art, the tensioned strip is likely to be scratched and qualitatively damaged, while in the solution according to the invention the strip, except in the gripped end, cannot be scratched as it does not come into contact with components of the unwinding system.

The shaped elements function as a jaw or a clamp and practically must be suitable to clamp the strip end therebetween, they must therefore securely retain the strip so as to accompany it with the bogie, avoiding the yielding of the strip as much as possible.

Also with its movement, preferably linear, along a guiding system, the bogie allows a long stroke to pull the strip and unwind it, while in the first system described in the state of the art the stroke is limited by the orientation radius of the pivoting arm determined by its geometry requiring a passage of the strip through the rollers for unwinding. A further advantage of the system according to the invention is the fact that the gripping element does not remain close to the coil, but moves together with the strip following the unwinding and thus allowing full access to the surface of the strip for its inspection. With respect to the version described in GB 988,334, where the strip is unwound from the top of the coil, in the present invention the strip can be unwound from the bottom of the coil thus arranging the inner surface of the strip upwards for inspection, for example a visual inspection.

With respect to the solutions of documents WO 2015/111028 A1 and IT 102014902227353, the design of the invention is much simpler and does not require complex components for detaching the strip from the coil and guiding it to the blocking system. In fact, the length of the strip portion which comes into contact with system components, a passage which can lead to surface defects in the quality of the strip, is thus reduced.

The reduced complexity allows considerable construction cost savings for producing the device and ensures system reliability and ease of operation. In fact, heavy components such as pressure rollers, leveling elements and their actuating units are not necessary. Avoiding pressure rollers and leveling elements avoids scratches on the surface of the strip which can also be caused by slips provoked by unsynchronized circumferential speeds of all the rollers involved in the transfer of the strip in the devices according to the state of the art. The proposed inventive concept helps during the unwinding to reduce the flattening of the strip end and to at least partially safeguard its original curve, allowing its rewinding, limiting damage to the surface and a residual spring effect.

In a preferred embodiment of the invention, said first and said second shaped element are rollers, providing a very simple system for inserting the strip in the blocking system. If both shaped elements are rollers, the first and the second roller preferably have parallel longitudinal axes at least in the gripping position. Preferably, the roller(s) forming the first shaped element and possibly also the second shaped element is/are an idler roller(s).

An alternative shape for the second shaped element can be a tilting flat plate adapted to follow the "natural" shape of the curved tail of the strip, having only a curved segment in the gripping area of the strip end. A preferred variant of the invention envisages the combination of a shaped element which is not a roller and a roller.

Advantageously, the element for detaching the strip end from the coil self-positions against the coil once the first shaped element comes into contact therewith. The peeling element, which can be a plate, a blade, a pin or the like, is in fact a shaped piece which serves as a guide for the portion of strip to be grasped. In this regard, it is implicit that the detachment element is placed on the lower part of the first shaped element resting on the coil.

The roller nature of the first blocking element allows a sliding of the strip along the blocking element and so as not to offer resistance to the rotation of the coil when resting thereon. The fact that the roller with the detachment element is therefore adapted to rest against the coil, contributes by virtue of the absence of the resistance to rotation of the coil to reduce the contact between portions of the strip and elements of the device itself as much as possible, as required by an object of the invention.

Advantageously, the actuating system comprises a pivotable arm, on which the second shaped element is mounted, and a mechanism for changing the orientation of the arm, preferably a pneumatic or hydraulic cylinder. The person skilled in the art easily identifies with his general knowledge other systems for changing the distance between the two shaped elements.

In an alternative embodiment, the pivotable arm can be replaced by a beam which makes a parallel movement towards the first shaped element to clamp the strip end.

Advantageously, the unwinding device according to the invention further comprises (a) a rotatable mandrel; and/or (b) support rollers, wherein, during use, a coil of a metal strip is wound on said rotatable mandrel and/or positioned on said support rollers, and wherein the mandrel and/or at least one support roller can be actuated. The non-actuatable support rollers are preferably idle rollers. Thereby the coil can be easily rotated to allow the unwinding of the strip, and this from the actuation of the mandrel and/or from at least one support roller.

A further aspect of the invention relates to a plant for inspecting a metal strip coming from a coil, comprising:

(a) an unwinding device according to the invention;

(ii) an inspection plane, placed along the guiding system, for supporting the unwound strip.

Preferably, the inspection plane is formed by a plurality of parallel rollers. Such a roller table or rather a roller path, or alternatively wheeled, allows a reduced friction support/sliding of the strip on a surface which can also be made of soft material, for example rubber or another synthetic or natural material preferably with low friction, to avoid scratches on the strip.

Preferably, the shaped elements are covered with soft rubber or polymeric materials in general.

In an advantageous embodiment of the invention, the inspection plant according to the invention further comprises:

(iii) an analysis device placed above the inspection plane and adapted to provide data on the surface quality of a strip resting on the inspection plane.

Camera, infrared, and other analytical devices which the expert can easily identify to obtain the desired information and automate the inspection process are imaginable. Once the analysis has been completed, the analysis system, in particular with a positive analysis result, can send a signal to the bogie and the coil rotation system to return the bogie to the coil and at the same time rewind the strip. The blocking system consisting of the two shaped elements releases the strip portion, preferably when the strip is rewound and the bogie is in the initial position, and is ready to grasp a new strip.

In preferred embodiments of the system, the inspection plant could contain cutting devices which cut portions of strip which will also be classifiable according to their surface quality based on the analysis results.

A third aspect of the invention relates to a method for unwinding a metal strip from a coil comprising the following steps:

(I) approaching a coil of a metal strip and an unwinding device according to the invention wherein the strip end is placed at a height lower than the height of the first shaped element and the second shaped element and wherein the opening angle between the strip end and the coil opens upwards;

(II) spacing the shaped elements;

(III) positioning the first shaped element and the element for detaching said strip end from the coil against the coil;

(IV) rotating the coil so as to carry the strip end upwards and to insert it between the first and the second shaped element;

(V) approaching the second shaped element to the first shaped element so as to grasp the strip end between both components of the blocking system; and (VI) translating the bogie along the guiding system and rotating the coil, unwinding the metal strip therefrom.

Steps (II) and (III) naturally do not follow a predetermined order dictated by the logic of the process, but can be in reversed order.

The term "high" is understood in reference to the support plane of the unwinding device, thus directed upwards from this plane, usually the floor. A system is also conceivable in which the strip end is placed at a height higher than the height of the first shaped element and the second shaped element and wherein the opening angle between the strip end and the coil opens downwards, thus towards the support plane of the device. In this case, with a strip detachment element located at the upper part of the first shaped element, the strip would be unwound from above, thus allowing to expose the outer surface of the strip for inspection, making it more difficult, however, to support the unwound strip.

An embodiment of the method according to the invention envisages that in step (VI) the unwound strip is preferably placed on an inspection plane and comprises a further step (VII) wherein the inner surface of the unwound strip is inspected for its surface quality.

This embodiment of the unwinding method transforms the method into a strip inspection method always comprising its unwinding from a relative coil.

In an advantageous embodiment of the invention, in step (V) the approach of the first shaped element and the second shaped element occurs with the actuating system comprising a pivotable arm, on which the second shaped element is mounted, and a mechanism for changing the orientation of the arm, preferably a pneumatic or hydraulic cylinder, where the mechanism changes the orientation of the pivotable arm and with this the distance between the two shaped elements.

Another embodiment of the unwinding and inspection method according to the invention can envisage after step (VII) a step (VIII) wherein the bogie returns towards the coil accompanied by a rotation of the coil to rewind the strip and a step (IX) wherein the second shaped element is spaced from the first to free the strip end. Subsequently, the previous steps can be repeated.

A final aspect of the invention proposes a use of the unwinding device or the inspection plant according to the invention for evaluating the wear of rolling cylinders used for producing the inspected strip. A poor quality of the strip, inspected according to the invention, can indicate a wear of the rolling cylinders which produced the strip. Obviously, the inspection could also detect defects of the strip due to other causes, such as poor strip material quality.

In a preferred embodiment of the method according to the invention, the surface quality of the inspected strip is used to evaluate the wear of the rolling cylinders used to produce the strip.

The features and advantages disclosed for one aspect of the invention may be transferred mutatis mutandis to the other aspect of the invention.

The industrial applicability is obvious from the moment when it becomes possible to simplify and make the unwinding and inspection of metal strips less complex, also allowing the inspection of the inner surface and reducing the risk of scratching the strip during the unwinding.

Said objects and advantages will be further highlighted during the description of preferred embodiments of the invention provided by way of example, without limitation.

Variants and further features of the invention are the object of the present application. The description of the preferred exemplary embodiments of the device, plant and method for unwinding a metal strip from a coil and a relative use according to the invention is given by way of non-limiting example, with reference to the attached drawings. In particular, unless specified otherwise, the number, shape, dimensions and materials of the system and of the individual components may vary, and equivalent elements may be applied without deviating from the inventive concept.

DETAILED DESCRIPTION

Figure 1:
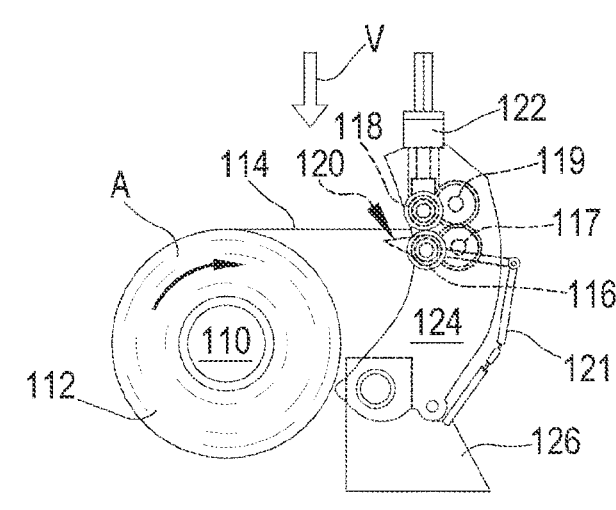
FIG. 1 shows a first system for unwinding metal strips from coils according to the prior art.
Figure 2:
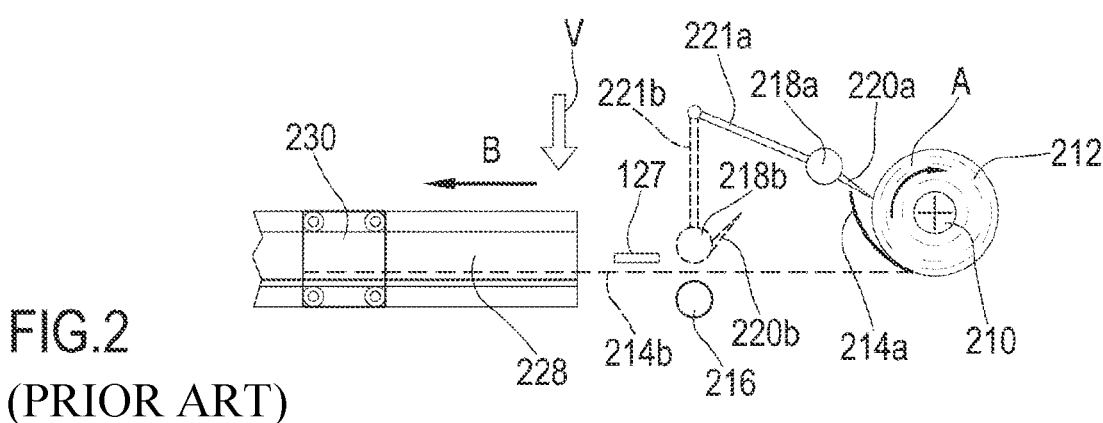
FIG. 2 shows a second system for unwinding metal strips from coils according to the prior art.

FIGS. 1 and 2 representing the prior art have already been initially explained.

Figure 3:
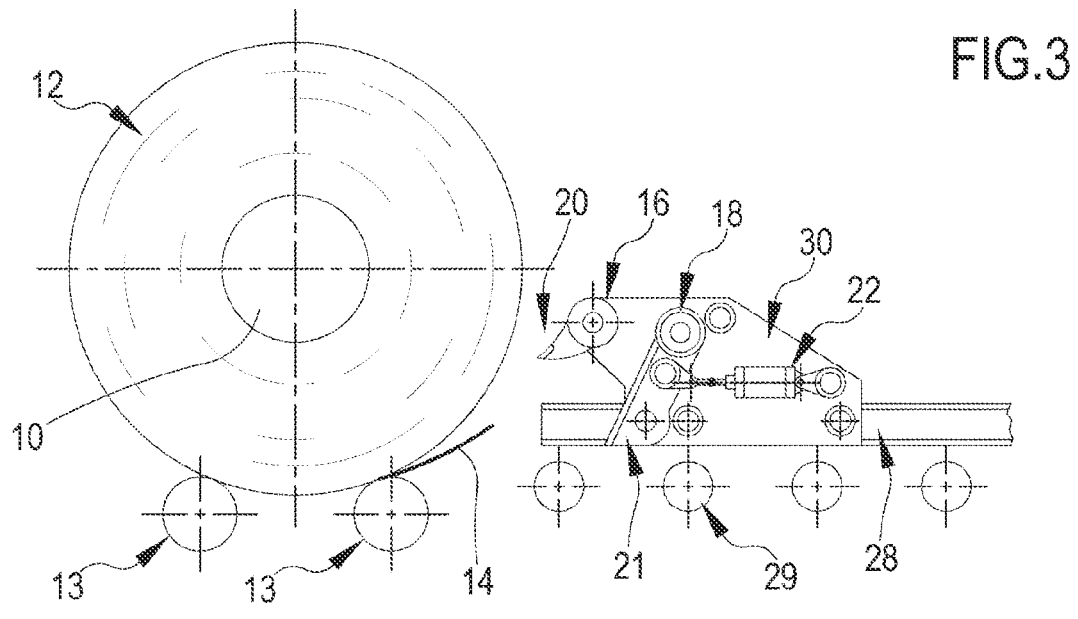
FIG. 3 shows an inspection system of metal strips according to the invention with a particular coil unwinding system.
Figures 4A, 4B, 4C, 4D, 4E:
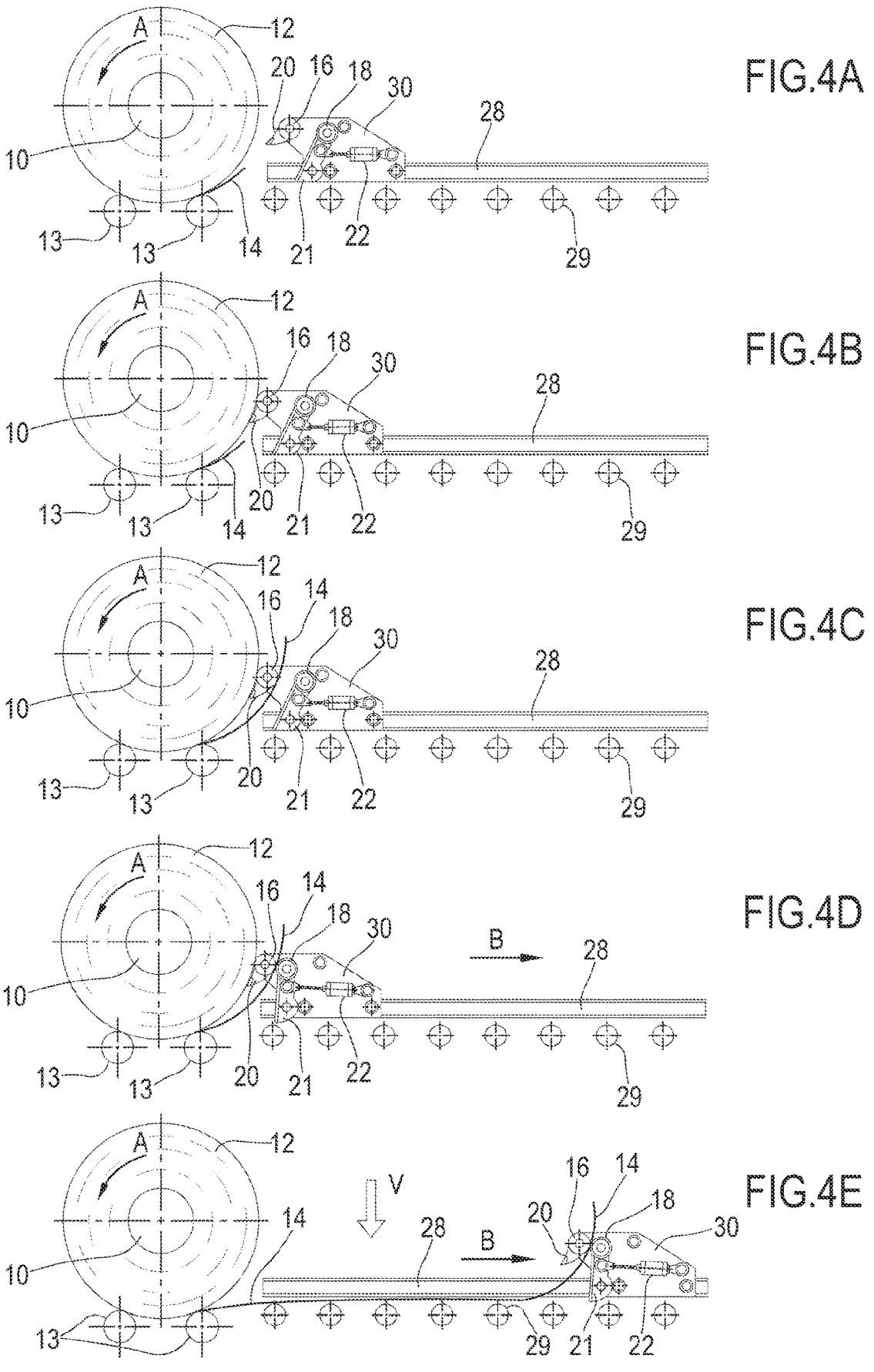
FIGS. 4A-4E show the succession of various steps of the coil unwinding method according to the invention for the surface inspection of the unwound strip.

FIG. 3 will instead be described below. It shows a system for inspecting coils of metal strips according to the invention with a particular coil unwinding system. A coil 12 of a metal strip is wound on an axis or motorized mandrel 10. The coil
12 is housed on two support rollers 13 of which at least one
can be motorized, while the other is preferably idle. As a
function of the rotation direction of the mandrel 10 and/or
the motorized support roller 13, the mandrel and/or the
support roller winds or unwinds the strip forming the coil 12.
Next to the coil 12, a roller path or a series of parallel rollers
29 for inspecting the unwound strip is envisaged. Only one
strip end 14, or tail, which is slightly detached from the coil
12, is noted in the present figure. Along the inspection table
29 there are guides 28 along which a bogie 30 moves. The
bogie 30 is provided on the side pointing towards the coil 12
with a strip detachment element 20 which is associated with
an idle roller 16. At about the same height as the idle roller
16, a second idle gripping roller 18 is mounted to a pivoting
arm 21 which can be actuated by a pneumatic or hydraulic
cylinder 22. The rotation of the pivoting arm 21 causes the
idle roller 18 to be approached to the other idle roller 16 so
as to trap the tail of the strip 14 in the middle.

FIGS. 4A to 4E show the sequence of the various steps of
unwinding a coil according to the invention for the surface
inspection of the unwound strip in which the system shown
in FIG. 3 is applied. The reference numbers correspond to
those of FIG. 3.

In the first step (FIG. 4A), the coil 12 is positioned on the
support rollers 13 so that the strip end 14 is (with the coil
seen in section) in the "4 o'clock" position with the strip end
14 indicating towards the blade-shaped detachment element
20. The bogie 30 is in the waiting position with the idle
gripping roller 18 open or spaced from the first idle roller 16.

In step two (FIG. 4B), the bogie 30 moves along the guide
28 towards the coil 12 to bring the roller 16 into contact with
the side surface of the coil 12. The detachment element or
the strip detachment tip is positioned, being associated with
the roller 16, independently against the coil 12.

In the third step (FIG. 4C), at least one support roller 13
and/or the mandrel 10 rotate to unwind the strip from the coil
12 and insert the strip end 14 between the unwinding roller
16 and the gripping roller 18.

Subsequently, in step four (FIG. 4D), the pneumatic or
hydraulic cylinder 22 pushes the pivoting arm 21 to grasp
the strip end 14 between the unwinding roller 16 and the
gripping roller 18, approaching the second 18 to the first 16.

In the final step five (FIG. 4E), the bogie 30 then moves
backwards in the direction of the arrow B and accompanies
the strip end 14 and thus the entire strip during its unwinding
carried out by the mandrel 10 and/or by a motorized support
roller 13. The unwound strip 14 extends on the roller path 29
and its inner surface (i.e., the concave surface which in the
rolled state indicated towards the inside of the coil 12) is
available for inspection (arrow V).

After the inspection, the above operations will be carried
out in reverse order, to roll the strip back on the coil 12, i.e.,
the bogie 30 moves towards the coil 12, the support roller 13
and/or the mandrel 10 rotate in the opposite direction to
support the winding of the strip 14, when the bogie 30 has
again reached the coil 12, the second roller 18 is distanced
from the first roller 16 by the movement of the cylinder 22,
the strip 14 exits the space between these two rollers 16 and
18, the bogie 30 and therewith the detachment element 20
and the relative idle roller 16 detach from the coil 12.

The invention claimed is:

1. A device for unwinding a coil of a metal strip com-
prising:
  (a) a bogie and a guiding system wherein the bogie is
    translatable back and forth along the guiding system;

(b) a blocking system which is arranged on said bogie and
    which contains a first shaped element and a second
    shaped element;
  (c) an actuating system for modifying the distance
    between said first and second shaped elements for
    defining an intercepting position of a strip end between
    said two shaped elements when spaced and a gripping
    position of said strip end by said two shaped elements
    when close together; and
  (d) an element for detaching said strip end from the coil
    provided on the first shaped element,
  wherein said element for detaching the strip end from the
    coil is positioned against the coil when the first shaped
    element contacts the coil, and
  wherein said first shaped element is a roller.

2. The device according to claim 1, wherein both said first
and said second shaped elements are rollers.

3. The device according to claim 1, wherein said roller
representing the first shaped element is an idle roller.

4. The device according to claim 1, wherein the element
for detaching the strip end from the coil is selected from a
plate, a blade, a pin.

5. The device according to claim 1, wherein said actuating
system is arranged on said bogie.

6. The device according to claim 1, wherein said actuating
system comprises a pivotable arm, on which said second
shaped element is mounted, and a mechanism for changing
the orientation of said arm.

7. The device according to claim 1, further comprising:
  (a) a rotatable mandrel; and/or
  (b) support rollers,
wherein, during use, the coil of the metal strip is wound on
said mandrel and/or placed on said support rollers and
wherein the mandrel and/or at least one support roller can be
actuated.

8. An inspection plant comprising:
  (i) the device for unwinding the coil of the metal strip
    according to claim 1; and
  (ii) an inspection plane, placed along said guiding system,
    for placing an unwound strip.

9. The inspection plant according to claim 8, further
comprising:
  (iii) an analysis device placed above said inspection plane
    adapted to provide data on the surface quality of a strip
    resting on said inspection plane.

10. A method for unwinding the metal strip from the coil
comprising the following steps:
  (I) approaching a coil of the metal strip and the device for
    unwinding according to claim 1, wherein the strip end
    is placed at a height lower than the height of the first
    shaped element and the second shaped element and
    wherein an opening angle between the strip end and the
    coil opens upwards;
  (II) spacing the shaped elements;
  (III) positioning the first shaped element and the element
    for detaching said strip end from the coil against the
    coil;
  (IV) rotating the coil so as to carry the strip end upwards
    and to insert it between the first and the second shaped
    element;
  (V) approaching the second shaped element to the first
    shaped element so as to grasp the strip end between
    both components of the blocking system; and
  (VI) translating the bogie along the guiding system and
    rotating the coil unwinding the metal strip therefrom,
  wherein step (II) and step (III) can reverse the order
    within the sequence of steps.

11. The method for unwinding the metal strip from the coil according to claim 10, wherein after step (VI) comprising a further step:

(VII) wherein an inner surface of the unwound strip is inspected for its surface quality.

12. The method for unwinding the metal strip from the coil according to claim 10, wherein in step (V) the approach of the first shaped element and the second shaped element occurs with the actuating system comprising a pivotable arm, on which the second shaped element is mounted, and a mechanism for changing the orientation of said arm, comprising at least one of a pneumatic or hydraulic cylinder.

13. The method for unwinding the metal strip from the coil according to claim 10, wherein the surface quality of the inspected strip is used for assessing the wear of rolling cylinders used for producing the inspected strip.

14. The device according to claim 6, wherein said mechanism for changing the orientation of said arm is a pneumatic or hydraulic cylinder.

15. The inspection plant according to claim 9, wherein the inspection plane comprises a plurality of parallel rollers for supporting the unwound strip to facilitate inspection of the unwound strip.

16. The method for unwinding the metal strip from the coil according to claim 11, wherein in step (VI) the unwound strip is placed on an inspection plane.

17. The device according to claim 2, wherein both rollers are idle rollers.

\* \* \* \* \*